United States Patent [19]

Renzi et al.

[11] 4,250,253

[45] Feb. 10, 1981

[54] COMPOSITION ADAPTED FOR THE DETERMINATION OF TRI-IODO THYRONINE AND DIAGNOSIS METHOD EMPLOYING SAME

[75] Inventors: Pierluigi Renzi; Vittorio Baroncelli, both of Rome, Italy

[73] Assignee: Snamprogetti S.p.A., Milan, Italy

[21] Appl. No.: 884,811

[22] Filed: Mar. 9, 1978

[30] Foreign Application Priority Data

Mar. 15, 1977 [IT] Italy ................ 21231 A/77

[51] Int. Cl.³ .................... C12Q 1/66; C12N 9/96
[52] U.S. Cl. ..................... 435/7; 435/188; 424/12
[58] Field of Search ............ 195/63, 68, 99, 103, 195/5 A; 252/408 R; 424/12; 23/230 B; 435/7, 188

[56] References Cited

U.S. PATENT DOCUMENTS

| | | | |
|---|---|---|---|
| 3,817,837 | 6/1974 | Rubenstein | 195/63 X |
| 3,850,752 | 11/1974 | Schuurs et al. | 195/63 |
| 4,040,907 | 8/1977 | Ullman et al. | 435/188 |

OTHER PUBLICATIONS

Wisdom, "Enzyme-Immunoassay," *Clin. Chem.*, vol. 22, No. 8, (1976), pp. 1243–1255.
Barman, *Enzyme Handbook*, vol. II, Springer–Verlag New York, Inc., New York, (1969) pp. 762–763.

*Primary Examiner*—Thomas G. Wiseman
*Attorney, Agent, or Firm*—Morgan, Finnegan, Pine, Foley & Lee

[57] ABSTRACT

A composition for diagnostic use is disclosed, more particularly for the dosage of tri-iodo thyronine in human blood serum: the subject composition comprises tri-iode thyronine as such and an enzyme which is covalently bonded to tri-iodo thyronine. A diagnostic method is also disclosed, which is intended for using the above specified composition in diagnostic runs. The method, briefly resumed, consists removing the tri-iodo thyronine of the serum sample being assayed by means of an insolubilized anti-$T_3$ antibody and treating the residue with the sensibilized enzyme which is nothing else than the covalent formed by tri-iodo thyronine and an appropriate enzyme, such as carbonic anhydrase.

1 Claim, 1 Drawing Figure

COMPOSITION ADAPTED FOR THE DETERMINATION OF TRI-IODO THYRONINE AND DIAGNOSIS METHOD EMPLOYING SAME

This invention relates to a novel composition which permits to carry into effect a diagnostic method for the determination of tri-iodo thyronine, said composition being constituted by an enzyme covalently bonded to the substance in question. The invention also relates to the diagnostic method as such.

It is known that there are a number of methods for the analysis of the tri-iodo thyronine, $T_3$ for short, and of its antibody, especially for their quantitative determination in blood serum.

Among these methods, the following may be mentioned:

(1) Measurement of the concentration of the total $T_3$ (a) Dosing by means of saturation analyses, which provide for the separation of the $T_3$ from thyroxine ($T_4$), such separation being actually cumbersome and being a serious hindrance to a routinely use.

(b) Radio-immunologic assay: at present, it is the most suitable method for the evaluation of tri-iodo thyronine. It provides for the use of a specific antibody and of $T_3$, the latter being labeled with $I_{125}$. The $T_3$ of the serum being assayed enters competition with the labeled-antibody $T_3$: the quantity of the complex $I_{125}$-$T_3$ is inversely proportional to the concentration of $T_3$ of the sample which is being tested. It should be emphasized, in connection with this method, that the compounds which are required, such as $I_{125}$, have a comparatively short life and that the test requires an expensive implementation. Furthermore, the use of radio-isotopes is subjected to a severe legislation by the Public Health Authority.

(2) Measurement of the interaction between hormone and TBP (Thyroxine-binding protein)

(a) Estimate of the free-hormone fraction by dialysis at the equilibrium, ultrafiltration, (b) estimate of the relative saturation of the thyroxine-binding sites: uptake by a resin of the labeled $T_3$ ($RT_3U$, i.e. Resin $T_3$ Uptake), (c) quantitative evaluation of the thyroxine-binding proteins: concentration of the TBG (thyroxine-binding globulin) and of the TBPA (thyroxine-binding prealbumin).

All these are laborious methods which are based on the binding ability of the TBP to the hormone, and give an indirect measure of the circulating $T_3$. The method which measures the uptake of the labeled $T_3$ by the resin is, summing up, the handiest of the three, even though it has the shortcomings already indicated at 1b, above.

By measuring the concentration of the total $T_3$ and of the interaction between the hormone and TBP, it is possible to calculate the concentration of the free $T_3$.

We have now found, and this is the subject-matter of the present invention, a method for the determination of tri-iodo thyronine which permits to dose it even in extremely small amounts, in the order of the nano-gram and under, without any of the shortcomings pointed out above, said method involving the use of an insolubilized antibody which is specific for $T_3$, and of a composition, which is also within the scope of the present invention, as supplied by a particular enzyme which is covalently bonded to same $T_3$ (sensibilized $E$-$T_3$ enzyme).

Insolubilization, as is known, permits to obtain immuno-absorbing antibodies which possess a high immunologic specificity and affinity. Using the composition indicated above, these properties are enhanced and, above all, the system acquires quite particular a stability, which is such as to permit to arrive at results which were wholly unpredictable in the light of the conventional knowledge: tri-iodo thyronine can be determined even if it is present in extremely tiny amounts and the reproducibility of the method is very high. This fact is the more note-worthy in that it is widely known that tri-iodo thyronine is an inhibitor of the enzymic activity of a few enzymes, such as lysozyme, with which it also forms an insoluble complex.

The selection of the enzyme of the immunoenzymic assay must be carried out according to the following criteria:

(a) The enzyme must possess a high specific activity at such a pH as not to loosen the antigen-antibody bond.

(b) The enzyme must be such as to be measured easily.

(c) The enzyme must be readily obtainable in a highly purified, soluble and stable form.

(d) The enzyme must possess reactive groups to which other molecules can be bonded without any loss of biological activity.

(e) The enzyme must not be inhibited by substances which are present in the blood-serum.

The determination, according to the method of this invention, is carried into constructive practice by extracting the $T_3$ of the sample being assayed with an affinity chromatography run on an insolubilized anti-$T_3$ antibody, the chromatography being carried out either in a column or in a test tube. By such a step a concentration of the substance being assayed is obtained and components which could possibly interfere with the analysis are removed. Subsequently, the column is treated with the solution of $E$-$T_3$ and the residual enzymic activity is determined in the effluent. If the sample does not contain substances to be dosed ($T_3$), the antibody blocks the sensibilized enzyme ($E$-$T_3$) and inhibits the activity of same. If, conversely, the substance is present, it will compete with the enzyme for the antibody, permitting that at least a part of the molecules of the latter may remain active.

From the foregoing, it appears that the immunoenzymic method of this invention for the determination of the tri-iodo thyronine is valid since it gives a direct measure of the circulating hormone, even if the latter is present at extremely low concentrations: such method, in addition, does not undergo any interference from substances which are present in the blood-serum, and can easily be performed.

It is apparent that our method can be employed for the determination of the anti-$T_3$ antibodies, inasmuch as it is sufficient to insolubilize the $T_3$, thereafter putting into contact with the insolubilized $T_3$, first the sample, and, then an enzyme which is covelently bonded to the anti-$T_3$. Lastly, the residual enzymic activity is measured: if the sample does not contain the antibodies, an $E$-$Ab.T_3$ complex will be the result, and the enzymic activity cannot be determined. If, conversely, antibodies are present in the sample, these will form a $T_3.Ab$ complex and it will be possible to determine the activity of the conjugated $E$-$Ab$.

Materials for the tests

The carbonic anhydrase and the bovine seroalbumin were products of the Böhringer-Mannheim Co. The 1-ethyl-3-(3-dimethylaminopropyl) carbodiimide was a product of Sigma. The 3,5,3'-triiodothyronine and the glutaraldehyde have been supplied by Fluka.

Test results

(A) Preparation of the anti-$T_3$ antibodies 50 milligrams (mg) of BSA (bovine seroalbumin) have been dissolved in 25 mls of water and 150 milligrams (mg) of 1-ethyl-3-(3-dimethylaminopropyl) carbodiimide have been added thereto. Subsequently, there have been added, dropwise, 100 mg of $T_3$, dissolved in 5 mls of N,N-dimethylformamide. After about 5 mins. there have been added 50 mg of 1-ethyl-3-(3-dimethylaminopropyl) carbodiimide.

The reaction has been allowed to proceed for 18 hours at room temperature, in the dark and with stirring. On completion of the reaction, the sample has been centrifuged and dialyzed against frequent renewals of distilled water for 72 hours. The number of residues of $T_3$ incorporated in each molecule of albumin was determined spectrophotometrically by using a coefficient of 6,100 $M^{-1}$ $cm^{-1}$ at 320 nm (nanometer). The results show that about 5 residues of $T_3$ were conjugated with each molecule of BSA. The UV-spectra of BSA and of the $T_3$-BSA conjugate are reported in the plots 1 and 2, respectively, of FIG. 1 of the accompanying drawing. The antibody has been obtained by sequential immunizations of rabbits with the $T_3$-BSA conjugate. To titrate the antibodies, the passive agglutination method has been used: this is a classic method of serology and consists in coating red blood cells, previously treated with tannic acid, with the antigen being assayed and then effecting an agglutination assay.

The antibody which has been obtained had a rating of 1:8,000. The purification of the antibody is carried out by centrifuging the serum and diluting the supernatant liquor with one volume of water and one volume of a saturated solution of ammonium sulfate, so as to obtain a final concentration of 33%. After 15 mins., the mixture has been centrifuged at 4,000 rpm for 20 mins. and the precipitate reslurried in a saline solution and precipitated again with ammonium sulfate until a complete decoloration of the solution had been obtained. The precipitate, taken up with a saline solution, has been dialyzed against two renewals (or thread of the saline solution at 4° C. until ammonium sulfate has completely been discharged.

(B) Preparation of the immuno-absorbing antibodies on polyacrylamide

The Bio-Gel P-300 was allowed to become hydrated for 24 hours in water and washed many times in the same medium. To 100 mls of the hydrated gel there were added 500 mls of a 6% solution of glutaraldehyde in a 0.1 M phosphate buffer at a pH of 7.0. The solution was incubated overnight at 37° C. The gel was then washed 10–20 times with water, using a 500-ml volume for each washing operation.

10 mls of activated gel were admixed with 12 mls of blood-serum. The solution was slowly stirred at room temperature for 14 hrs., centrifuged at 3,000 rpm for 10 mins., at 4° C. and the supernatant liquor removed to evaluate the quantity of antibody which had not been absorbed. The particles of the gel were then washed with an isotonic buffer until the optical density of the supernatant liquor was less than 0.02 at 280 nm. The quantity of antibody which had been conjugated was 23 mg per ml of gel.

(C) Preparation of the $T_3$-carbonic anhydrase conjugate ($T_3$.BCA)

50 mg of carbonic anhydrase have been dissolved in 25 mls of water and admixed with 30 mg of 1-ethyl-3-(3-dimethylaminopropyl carbodiimide, 20 mg of $T_3$, dissolved in 5 mls of N,N-dimethylformamide have been added dropwise, the pH being maintained between 5.5 and 6.0. The solution was kept with constant stirring at room temperature, in the dark, for about 18 hrs. On completion of this step, the sample was centrifuged and dialyzed against frequent renewals of water at 4° C. for about 48 hrs. The spectrophotometric analysis showed than a residue of $T_3$ had been conjugated with one molecule of carbonic anhydrase. The residual enzymic activity of the conjugate was correspondent to about 50% of that of the native enzyme. The $T_3$-BCA conjugated was homogeneous and different from the native enzyme as it was checked by electrophoresis.

(D) Determination of $T_3$

A calibration curve is plotted, at the outset, according to the following procedure: 1 ml of antibody insolubilized on Bio-Gel P-300 is placed on a column (0.5 by 5.0 cm), thermostatically kept at 25° C. Through the column 1 ml of a solution containing the $T_3$-BCA conjugate at a concentration of 0.5 M is caused to run. The column is allowed to stand for one hour, then it is washed with 1 ml of isotonic solution and, on the effluent, the residual biological activity of the conjugate is determined. The biological activity of the $T_3$-BCA conjugate is determined spectrophotometrically at 25° C. by measuring the increase of the absorption of 348 nm due to the hydrolysis induced by p.nitrophenyl acetate. 1 ml of the effluent is admixed with 1 ml of 3 millimolar (mM) p.nitrophenylacetate solution, 0.3 ml of 20mM phosphate buffer (pH 7.4), and 0.7 ml water. In the standard cell a blank is placed which contains all the reagents, the enzyme being excepted. For the determination of tri-iodo thyronine, gradually increased quantities of free hormone (from 3 to 70 nanograms per milliliter) are placed in various columns which contain, each, 1 ml of insolubilized antibody, the test vessels being allowed to stand for one hour. The resin is washed with 5 mls of isotonic solution (buffer), eluted again with 1 ml of 0.5 micromolar $T_3$-BCA and allowed to stand for one hour. The resin is washed again with 1 ml of isotonic buffer and, on the effluent, the specific activity of the $T_3$-BCA conjugate is determined. FIG. 2 of the accompanying drawings reports the trend of the specific activity of the $T_3$-BCA conjugate as a function of the concentration of free $T_3$ (abscissae). The minimum quantity which can be measured is 1 to 2 nanograms.

(E) Determination of $T_3$ in standard human blood sera

With the procedure set forth above, there have been analyzed three standard sera of hypo-, eu- and hyperthyroidal patients, the following values having been obtained, respectively: 110 nanograms per 100 mls-236 nanograms per 100 mls-500 nanograms per 100 mls. These values are in good agreement with those measured by utilizing radio-immunological assays. The specificity of the antibody as obtained by this invention has been evaluated by measuring the ability of the $T_4$ in competing with $T_3$ for the antiserum. To obtain a variation of the specific activity of the $T_3$-BCA conjugate which was equivalent to that induced by 2 nanograms of $T_3$, 500 micrograms of $T_4$ are required. On considering that the normal concentration of $T_4$ in the human blood serum is about 80 nanograms per milliliter its interference in the measuring system is negligible.

Figure 1:
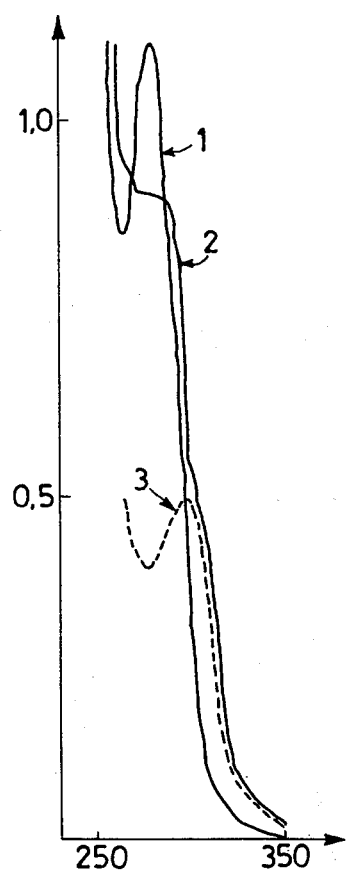
FIG. 1 is a UV spectrum of the serum albumin (bovine) and the $T_3$-bovine serum albumin conjugate in aqueous solution. Plot 1 is the plot for bovine serum albumin alone. Plot 2 is that for the $T_3$-bovine serum albumin conjugate. Plot 3 is the differential spectrum of the conjugate less the bovine serum albumin.
Figure 2A:
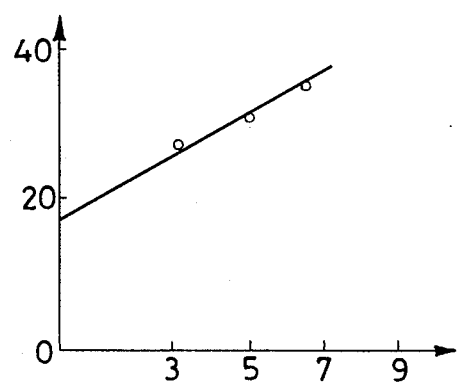
FIG. 2 shows the percentage variation of the activity of the conjugate $T_3$-carbonic anhydrase as a function of the concentration of free $T_3$. The curve (a) is for the range from 0 to 7 nanograms per milliliter and the curve (b) is for the range from 0 to 70 nanograms per milliliter. The activity was determined as set forth hereinabove.
Figure 2B:
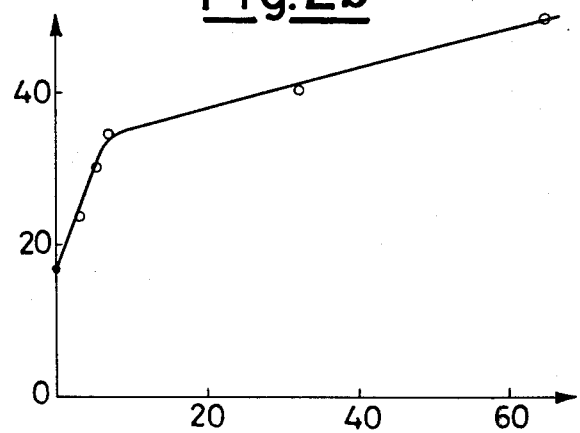

We claim:

1. A method for the determination of the concentration of tri-iodo thyronine said method comprising:
    (a) extracting the tri-iodo thyronine of the sample being assayed by means of an insolubilized anti-$T_3$ antibody derived from serum and tri-iodo thyronine;
    (b) contacting the extracted tri-iodo thyronine in a column with a sensibilized enzyme that is an enzyme that is covalently with tri-iodo thyronine and is derived from carbonic anhydrase and tri-iodo thyronine;
    (c) hydrolyzing the effluent from the column with p-nitrophenylacetate; and
    (d) spectrophotometrically determining the concentration of tri-iodo thyronine by measuring the absorption of p-nitrophenylacetate hydrolyzed washings from said column in comparison with a standard.

* * * * *